United States Patent
Graf et al.

(10) Patent No.: US 11,424,037 B2
(45) Date of Patent: Aug. 23, 2022

(54) DISEASE SIMULATION IN MEDICAL IMAGES

(71) Applicant: International Business Machines Corporation, Armonk, NY (US)

(72) Inventors: Benedikt Graf, Charlestown, MA (US); Arkadiusz Sitek, Ashland, MA (US); Yiting Xie, Cambridge, MA (US); Amin Katouzian, Lexington, MA (US); Pedro Luis Esquinas Fernandez, Etobicoke (CA); Lilla Boroczky, Mount Kisco, NY (US); Mark D. Bronkalla, Waukesha, WI (US)

(73) Assignee: International Business Machines Corporation, Armonk, NY (US)

( * ) Notice: Subject to any disclaimer, the term of this patent is extended or adjusted under 35 U.S.C. 154(b) by 201 days.

(21) Appl. No.: 16/691,853

(22) Filed: Nov. 22, 2019

(65) Prior Publication Data

US 2021/0158971 A1    May 27, 2021

(51) Int. Cl.
| | |
|---|---|
| *G16H 50/50* | (2018.01) |
| *G16H 30/20* | (2018.01) |
| *G06N 3/08* | (2006.01) |
| *G06K 9/62* | (2022.01) |
| *G16H 30/40* | (2018.01) |

(52) U.S. Cl.
CPC ........... *G16H 50/50* (2018.01); *G06K 9/6256* (2013.01); *G06N 3/08* (2013.01); *G16H 30/20* (2018.01); *G16H 30/40* (2018.01); *G06V 2201/03* (2022.01)

(58) Field of Classification Search
CPC .................. G06Q 50/22–24; G16H 50/50
See application file for complete search history.

(56) References Cited

U.S. PATENT DOCUMENTS

| | | | |
|---|---|---|---|
| 8,634,622 B2 | 1/2014 | Woods et al. | |
| 9,916,679 B2 | 3/2018 | Flynn et al. | |
| 10,448,911 B2 * | 10/2019 | Erhard | A61B 6/466 |

(Continued)

FOREIGN PATENT DOCUMENTS

| | | |
|---|---|---|
| CN | 107464234 A | 12/2017 |
| CN | 108538112 A | 9/2018 |

(Continued)

OTHER PUBLICATIONS

Forward and backprojection model; Y. Levakhina; Three Dimensional Digital Tomosynthesis; 2014 (Year: 2014).*

(Continued)

*Primary Examiner* — John A Pauls
(74) *Attorney, Agent, or Firm* — Timothy J. Singleton

(57) ABSTRACT

A method, system, and computer program product provide disease simulation in synthetic projection imagery. The method obtains first medical imaging data of a first imaging type as source imaging data. A second imaging type to be generated from the source imaging data is identified. The method identifies a parameter set for the second imaging type. Second medical imaging data is modeled from the first medical imaging data based on the parameter set. A set of synthetic images is generated from the first medical imaging data based on the modeled second medical imaging data.

17 Claims, 6 Drawing Sheets

(56) References Cited

U.S. PATENT DOCUMENTS

| | | | |
|---|---|---|---|
| 2008/0118020 A1* | 5/2008 | Thibault | G06T 11/006 378/4 |
| 2015/0042658 A1* | 2/2015 | Erhard | G06T 5/002 345/427 |
| 2015/0330915 A1* | 11/2015 | Jin | G01N 23/225 378/62 |
| 2017/0024634 A1 | 1/2017 | Miao et al. | |
| 2017/0316588 A1* | 11/2017 | Homann | G06T 11/008 |
| 2017/0357844 A1 | 12/2017 | Comaniciu | |
| 2017/0364145 A1 | 12/2017 | Blum et al. | |
| 2018/0071452 A1* | 3/2018 | Sharma | G16H 30/40 |
| 2018/0144550 A1 | 5/2018 | Vaxman et al. | |
| 2018/0197048 A1* | 7/2018 | Micks | H04N 13/275 |
| 2018/0204315 A1* | 7/2018 | Plihal | G06T 7/001 |
| 2018/0247227 A1* | 8/2018 | Holtham | G06K 9/6215 |
| 2021/0383538 A1 | 12/2021 | Deasy | |

FOREIGN PATENT DOCUMENTS

| | | |
|---|---|---|
| CN | 108765417 A | 11/2018 |
| WO | 2018048507 A1 | 3/2018 |
| WO | 2019245597 A1 | 12/2019 |

OTHER PUBLICATIONS

Alaei et al., "Imaging dose from cone beam computed tomography in radiation therapy", Physica Medica, 2015, 13 pages, Review paper.

Berthon et al., "PETSTEP: Generation of synthetic PET lesions for fast evaluation of segmentation methods", Physica Medica, Received May 26, 2015, 12 pages. https://www.sciencedirect.com/science/article/pii/S1120179715003130.

Jin et al., "CT-Realistic Lung Nodule Simulation from 3D Conditional Generative Adversarial Networks for Robust Lung Segmentation", arXiv:1806.04051 v1 [cs.CV] Jun. 11, 2018, 8 pages.

Lau et al., "ScarGAN: Chained Generative Adversarial Networks to Simulate Pathological Tissue on Cardiovascular MR Scans", 2018 SIIM Conference on Machine Intelligence in Medical Imaging, Sep. 9-10, 2018, Hilton SF Financial District | San Francisco, CA, 3 pages.

Litjens et al., "Simulation of Nodules and Diffuse Infiltrates in Chest Radiographs Using CT Templates", MICCAI 2010, Part II, LNCS 6362, 2010, copyright Springer-Veriag Berlin Heidelberg 2010, 9 pages. https://www.researchgate.net/publication/46818733_Simulation_of_Nodules_and_Diffuse_Infiltrates_in_Chest_Radiographs_Using_CT_Templates.

Moore et al., "A method to produce and validate a digitally reconstructed radiograph-based computer simulation for optimisation of chest radiographs acquired with a computed radiography imaging system", The British Journal of Radiology vol. 84, (2011), 13 pages. https://www.ncbi.nlm.nih.gov/pmc/?term=3473768.

Moturu et al., "Creation of Synthetic X-Rays to Train a Neural Network to Detect Lung Cancer", Department of Computer Science, University of Toronto, Canada, Aug. 20, 2018, 16 pages.

Salehinejad et al., "Generalization of Deep Neural Networks for Chest Pathology Classification in X-Rays Using Generative Adversarial Networks", This paper is accepted for presentation at IEEE International Conference on Acoustics, Speech and Signal Processing (IEEE ICASSP), 2018, arXiv:1712.01636v2 [cs.CV] Feb. 12, 2018, 5 pages. https://arxiv.org/abs/1712.01636.

Shin et al., "Medical Image Synthesis for Data Augmentation and Anonymization using Generative Adversarial Networks", arXiv:1807.10225v2 [cs.CV] Sep. 13, 2018, 11 pages.

List of IBM Patents or Patent Applications Treated as Related, dated Nov. 22, 2019, 2 pages.

Graf et al., "Disease Simulation and Identification in Medical Images", U.S. Appl. No. 16/691,824, filed Nov. 22, 2019.

Zhao et al., "Tumor Co-Segmentation in PET/CT using Multi-Modality Fully Convolutional Neural Network," Physics in medicine and biology, vol. 64,1 015011, Dec. 21, 2018, doi:1088/1361-6560/aaf44b, 28 pages, <https://www.ncbi.nlm.nih.gov/pmc/articles/PMC7493812/>.

* cited by examiner

DISEASE SIMULATION IN MEDICAL IMAGES

BACKGROUND

Neural networking algorithms are employed in many areas of data analysis. Neural networking and deep learning algorithms have been used in image recognition. Such algorithms employ large data sets for training of neural networking models used to perform data analysis, such as image recognition. The data sets are often labeled to designate attributes of interest within individual or groups of discrete files within the data sets. The size and quality of data sets used for training, tuning, and testing of neural networking algorithms often materially affect the quality and precision of the neural networking models.

SUMMARY

According to an embodiment described herein, a computer-implemented method for disease simulation in synthetic projection imagery is provided. The method obtains first medical imaging data of a first imaging type as source imaging data. A second imaging type to be generated from the source imaging data is identified. The method identifies a parameter set for the second imaging type. Second medical imaging data is modeled from the first medical imaging data based on the parameter set. A set of synthetic images is generated from the first medical imaging data based on the modeled second medical imaging data.

According to an embodiment described herein, a computer-implemented method for disease simulation in synthetic projection imagery includes generating one or more imaging attributes for the second medical imaging data. the one or more imaging attributes represent one or more medical imaging abnormalities. The computer-implemented method inserts the one or more imaging attributes into one or more synthetic images of the set of synthetic images. According to embodiments described herein, a system and a computer program product are described which are similar to or the same as the above-referenced computer-implemented method.

According to an embodiment described herein, a system for disease simulation in synthetic projection imagery is provided. The system includes one or more processors and a computer-readable storage medium, coupled to the one or more processors, storing program instructions that, when executed by the one or more processors, cause the one or more processors to perform operations. The operations obtain first medical imaging data of a first imaging type as source imaging data. A second imaging type to be generated from the source imaging data is identified. The operations identify a parameter set for the second imaging type. Second medical imaging data is modeled from the first medical imaging data based on the parameter set. A set of synthetic images is generated from the first medical imaging data based on the modeled second medical imaging data.

According to an embodiment described herein a computer program product for disease simulation in synthetic projection imagery is provided. The computer program product includes a computer readable storage medium having program instructions embodied therewith, the program instructions being executable by one or more processors to cause the one or more processors to perform operations including obtaining first medical imaging data of a first imaging type as source imaging data. A second imaging type to be generated from the source imaging data is identified. The computer program product identifies a parameter set for the second imaging type. Second medical imaging data is modeled from the first medical imaging data based on the parameter set. A set of synthetic images is generated from the first medical imaging data based on the modeled second medical imaging data.

DETAILED DESCRIPTION

Figure 1:
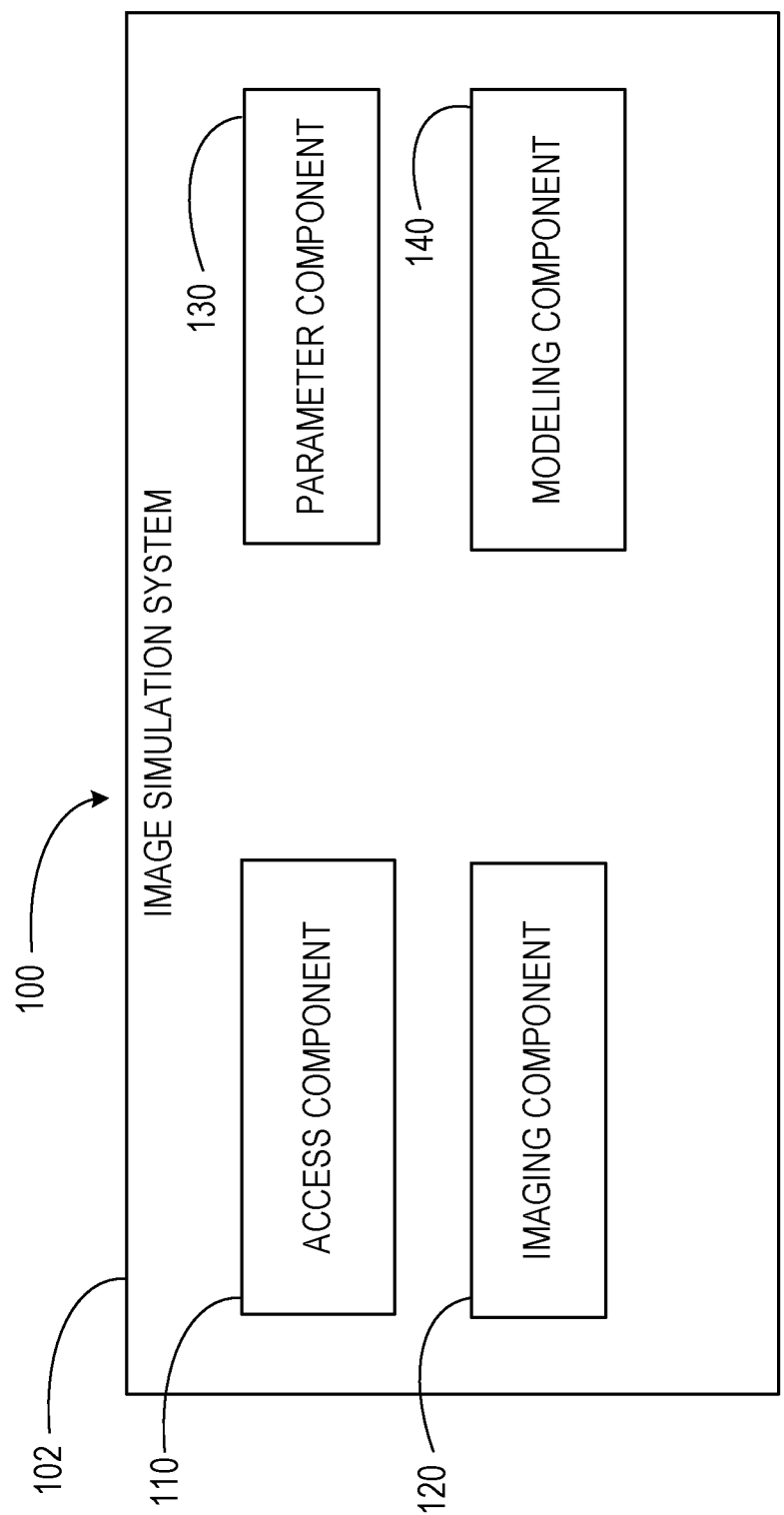
FIG. 1 depicts a block diagram of a computing environment for implementing concepts and computer-based methods, according to at least one embodiment.

The present disclosure relates generally to methods for disease simulation in synthetic projection imagery. More particularly, but not exclusively, embodiments of the present disclosure relate to a computer-implemented method for volumetric-to-planar data augmentation for synthetic projection imagery in medical imaging. The present disclosure relates further to a related system for disease simulation in medical imagery, and a computer program product to provide such a system.

Computer learning (e.g., neural networking and deep learning algorithms) is used across various applications for analyzing data sets. Computer learning systems may generate models from large and organized data sets. In some industries and applications, sufficiently large data sets have been collected for training varying types or aspects of neural networking models. Collecting large data sets in the medical imaging domain presents challenges distinct from other applications or fields. A prevalence of some diseases may be low, precluding collection of large and varied data sets relating to those diseases. Additionally, there may be a relatively wide variability of images that include and/or indicate a disease. The variability of such "positive" images may be attributed to timing of a diagnosis or imaging of the disease, peculiarities of patients having the disease (e.g., natural differences in tissue/organ/bone shapes and/or locations), location variation of diseases, and differences in severity of a specified disease. Similarly, technical aspects may affect the variability in imaging diseases. These technical factors may include patient position, scanner or imaging model, image acquisition and reconstruction parameters, combinations thereof, and other pertinent factors. As such, training neural networking models on data sets with sufficient variability may present significant challenges.

As an example, pneumothorax is a condition which consists of air leaking into the pleural space of a chest cavity.

This condition may be detected using chest x-rays. The prevalence of pneumothorax in chest x-rays is typically one to three percent. The appearance of the pneumothorax on x-ray images varies significantly. The variance may be attributable to a size of the impacted area of the patient, ranging from small pockets of air to a total collapse of a lung with a large volume in a chest cavity occupied by air. Further, variability may occur due to patient positioning. For example, intrathorax air pockets may accumulate in different parts of the chest cavity, based on a patient's position. The positioning may make the air pockets appear differently on x-rays. Additionally, image quality of x-rays may vary. A wide range of image quality for chest x-rays may be experienced due to variations in positioning of the x-ray source with respect to patient and the detector, an energy spectrum of the source, particularities of a patient, x-ray dose and noise, whether or not an anti-scatter grid is used or not, and the detectors used. Thus, building a data set of pneumothorax images may present difficulties in shared attributes suitable for modeling and identification in later patient images.

By way of further example, differences in patient and detector positioning introduce acquisition variabilities to medical imaging. Cases where a detector and patient are not squarely aligned may result in blurring, structure distortion, or non-standard structure overlap such as in the mediastinum. Patient positioning errors may result in medical images being rotated, clipped, or otherwise distorted. Portable imaging devices, such as portable or upright chest x-rays, may be taken with a patient in a sitting position facing away from a detector. Portable imaging devices may take supine images (e.g., patients laying on a table or bed) but may generate poorer quality images due the variabilities of placement and orientation of the imaging device and patient within a non-standard imaging room. Each of these images, errors, or variances may be simulated by embodiments of the present disclosure.

Embodiments of the present disclosure enable collection of significantly large data sets for model generation by using medical images as a starting point. Synthetic images are generated from medical imaging data. Embodiments of the present disclosure enable simulation of diseases and abnormalities in medical images to generate training samples to improve training of image analytics and image recognition algorithms and models. The synthetic images may be generated by introducing abnormalities of interest using image processing operations including segmenting and reshaping portions of images, introducing foreign objects, introducing voids, combinations thereof, and any other suitable modification of medical images. For example, synthetic chest x-rays may be generated for training deep learning models used for automated or semi-automated disease identification. The present disclosure enables generation of two-dimensional projection simulations (such as projection x-ray simulations) from three-dimensional medical image data, (such as CT scans). The two-dimensional simulations may be projected CT volume data into planar x-ray images. Synthetic projection images, using embodiments of the present disclosure, enable generation of synthetic projection images from volumetric CT data to generate training samples for deep learning models applicable to radiation-based medical imaging, such as two-dimensional x-ray images, or two-dimensional or three-dimensional nuclear medicine images, such as 18F-FDG PET scans. Embodiments of the present disclosure enable reductions in time, expense, and computing cycles in collecting medical images and generating models. Further, embodiments of the present disclosure enhance accuracy and precision of imaging models in detecting abnormalities within patient medical images.

Synthetic images can also be generated without simulating disease or abnormalities. In this case, the three-dimensional images can provide more information about the extent of the abnormality or disease than a two-dimensional projection image. The information from the three-dimensional images can be used as a more stable and reliable foundation or ground truth for the training of the models with the synthetic projection images.

Some embodiments of the concepts described herein may take the form of a system or a computer program product. For example, a computer program product may store program instructions that, when executed by one or more processors of a computing system, cause the computing system to perform operations described above with respect to the computer implemented method. By way of further example, the system may comprise components, such as processors and computer readable storage media. The computer readable storage media may interact with other components of the system to cause the system to execute program instructions comprising operations of the computer implemented method, described herein. For the purpose of this description, a computer-usable or computer-readable medium may be any apparatus that may contain means for storing, communicating, propagating, or transporting the program for use, by, or in connection with, the instruction execution system, apparatus, or device.

Referring now to FIG. 1, a block diagram of an example computing environment 100 is shown. The present disclosure may be implemented within the example computing environment 100. In some embodiments, the computing environment 100 may be included within or embodied by a computer system, described below. The computing environment 100 may include an image simulation system 102. The image simulation system 102 may comprise an access component 110, an imaging component 120, a parameter component 130, and a modeling component 140. The access component 110 obtains medical imaging data and user inputs to generate synthetic images. The imaging component 120 identifies imaging types and generates synthetic images. The parameter component 130 identifies parameters based on which synthetic images are generated. The modeling component 140 models second medical imaging data from medical imaging data obtained by the access component 110. Although described with distinct components, it should be understood that, in at least some embodiments, components may be combined or divided, or additional components may be added, without departing from the scope of the present disclosure.

Figure 2:
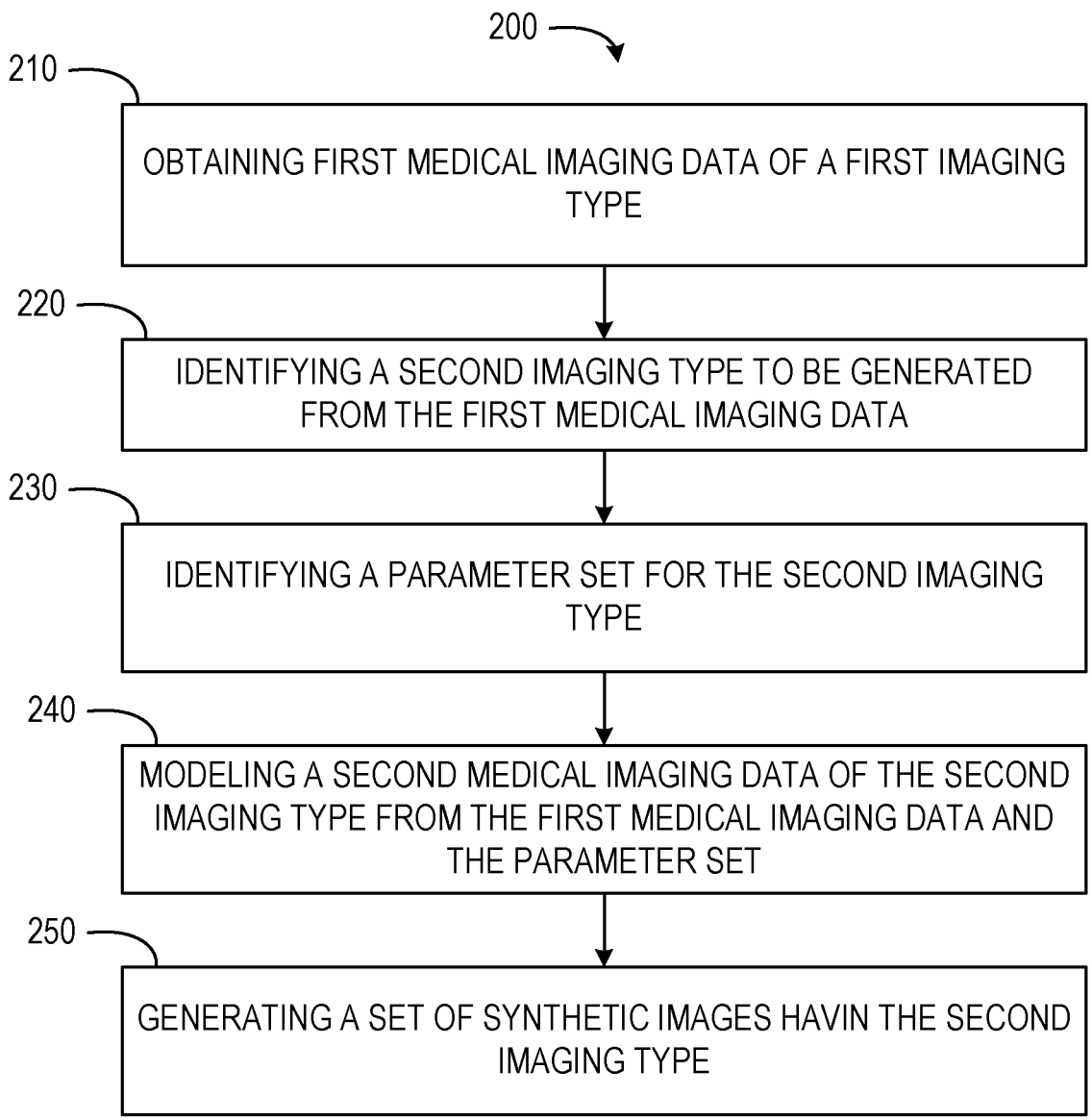
FIG. 2 depicts a flow diagram of a computer-implemented method for disease simulation in synthetic projection imagery, according to at least one embodiment.

Referring now to FIG. 2, a flow diagram of a computer-implemented method 200 is shown. The computer-implemented method 200 is a method disease simulation in synthetic projection imagery. In some embodiments, the computer-implemented method 200 may be performed by one or more components of the computing environment 100, as described in more detail below.

At operation 210, the access component 110 obtains first medical imaging data as source imaging data. The first medical imaging data may be of a first imaging type. In some embodiments, the first imaging type is volumetric computerized tomography (CT) scan data. The first medical imaging data may be scan data of healthy tissue, diseased tissue, damaged tissue, combinations thereof, or any other suitable and relevant scan data. In some embodiments, the first medical imaging data is a single image. For example, the first medical imaging data may be a single volumetric CT scan of a specified portion of a body.

The access component 110 may obtain the first medical imaging data from an imaging repository. In some embodiments, the access component 110 obtains the first medical imaging data from an imaging device, such as a computerized tomography scanner, a computerized axial tomography scanner, or any other suitable scanning or imaging device. In some embodiments, a user interface is presented on a computing device. A user may select the first medical imaging data or search for the first medical imaging data. In response to user selections or search queries within the user interface, the access component 110 may select the first medical imaging data from a set of medical imaging data within an imaging repository.

At operation 220, the imaging component 120 identifies a second imaging type to be generated from the source imaging data. In some embodiments, the first imaging type is distinct from the second imaging type. In some embodiments, the second imaging type is x-ray data. Where the second imaging type is x-ray data or other two-dimensional imaging, such as two-dimensional (e.g., planar) nuclear medicine imaging data, and the first imaging type is three-dimensional nuclear medicine imaging data, such as positron emission tomography scan data, embodiments described herein may generate simulated images of the second imaging type from the first imaging type.

The second imaging type may also be nuclear medicine imaging data, such as single positron computed emission tomography (SPECT) or Fludeoxyglucose (18F-FDG) positron emission tomography (PET) scan data. In such embodiments, to generate synthetic images of the second imaging type (e.g., SPECT or PET) from the first imaging type (e.g., volumetric CT data), embodiments of the present disclosure may simulate a synthetic radiotracer distribution within a region of interest in the volumetric CT data. For example, 18F-FDG may be simulated as uniformly distributed within a bladder. Embodiments of the present disclosure may then simulate emission of photons from the region (e.g., photons traveling from the bladder, through tissue, to the PET detector) to obtain planar data (e.g., i.e., planar nuclear medicine projection data). Once the planar data is obtained, three-dimensional PET/SPECT synthetic images may be reconstructed from these projections. Although described with respect to specified imaging types, it should be understood that the first imaging type and the second imaging type may be any suitable or relevant medical imaging data, scan data, or imaging types.

In some embodiments, the imaging component 120 identifies the second imaging type as a selection within a user interface. After selecting or searching for the first imaging data, the user may be prompted to identify the second imaging type. The user may select the second imaging type, such as x-ray data, from a set of imaging types. Once selected, the imaging component 120 identifies the selection as the second imaging type to which the first imaging data will be converted for generating synthetic images. In some embodiments, the imaging component 120 performs batch operations, automating generation of sets of synthetic images. The batched generation of synthetic images may be based on a set or corpus of source images (e.g., hundreds or thousands of images), parameter sets generated or selected for each batch, and automatically generated, as described in more detail below. Parameter sets, as discussed below, may enable multiple variations for each source image or source image set to generate one or more simulated output images. As discussed herein, the embodiments of the present disclosure may enable automatic or semi-automatic generation of any number of synthetic images (where automatic means without human guidance, prompting, and/or supervision). For example, the present disclosure may generate a single synthetic image, hundreds of synthetic images, or thousands of synthetic images with sets of synthetic images including one or more of the generated images.

At operation 230, the parameter component 130 identifies a parameter set for the second imaging type. The parameter component 130 may identify the parameter set as one or more selections of a user within a user interface presented by the image simulation system 102. In some embodiments, the parameter set includes physical properties or aspects of one or more of a target imaging device or the second imaging type. The target imaging device may be an imaging device configured to capture medical images of the second imaging type. In some embodiments, the parameter set includes a sensitivity, a resolution, a noise, a noise ratio, x-ray source to detector geometry (e.g., a source to image distance), orientation of the patient image volume within the x-ray geometry (affecting rotations and geometric magnification of the structures), x-ray beam attenuation characteristics, combinations thereof, or any other suitable and relevant physical properties or parameters.

By selecting and adjusting the parameter set, the components of the image simulation system 102 may control and modify forward projection parameters for converting CT scans to x-rays. Further, selection and adjustment of the parameter set enable generation of a large variety of images, of the second imaging type, from a single first medical image or medical image data. The generation of large and varied synthetic image data enables improvement in performance of deep learning models from a single medical image. By modeling detector geometry and physical properties of differing imaging devices or imaging device manufacturers into a forward projection of the first medical imaging data, the imaging simulation system 102 may be used to increase generalization of deep learning models that may be applied by differing imaging centers, imaging manufacturers, or users.

In some embodiments, selection and adjustment of the parameter set may correct for, manipulate, or simulate scan parameters for two-dimensional medical images, such as x-rays. In some instances, selecting and adjusting the parameter set is applied to emulate different image capture settings such as portable chest x-rays taken laying down in the bed, sitting upright in a recliner or as a standing chest x-ray in a radiology department or facility. Each setting contributes to variations in alignment of the x-ray geometry and patient. Further, the orientation of the patient may cause shifts in the relative position of the various internal structures (e.g., organs or skeletal structures) which can also be modeled and used in the creation of the resulting images. Selection and adjustment of the parameter set may be used to provide a framework for creating simulated images of specified orientations, image capture settings, and other relevant and suitable aspects of medical images.

At operation 240, the modeling component 140 models a second medical imaging data of the second imaging type from the imaging data of the first imaging type based on the parameter set. In some embodiments, the modeling component 140 models the second medical imaging data using forward projection operations. The modeling component 140 may use forward projection analytical models, Monte-Carlo or statistical methods, combinations thereof, or any other suitable and relevant forward projection methods or operations. In some instances, the modeling component 140 combines forward projection operations with deep learning models to model the second medical imaging data. For example, in an x-ray imaging system, forward projection operations may model emissions of x-rays from an x-ray tube, through patient anatomy, to a detector. In nuclear medicine systems, the forward projection operations may model emission of gamma rays from a radioactive source, present within a patient, through the patient anatomy to a detector.

In some embodiments, modeling the second medical imaging data converts a first dimensionality of the first medical imaging data to a second dimensionality of the second medical imaging data. The first dimensionality may be three-dimensional, such that the first medical imaging data is a three-dimensional imaging data or scan. The second dimensionality may be two-dimensional, such that the second medical imaging data is a two-dimensional imaging data or scan. For example, where the first medical imaging data is CT scan data and the second medical imaging data is x-ray data, the modeling component 140 models x-ray data from the CT scan data. In some embodiments, modeling the second medical imaging data and converting dimensionality of the first medical imaging data, enables generation of tomosynthesis x-ray images from volumetric CT scan data. In such instances, the modeling component 140 may use linear tomography or tomosynthesis for converting dimensionality for generation of the tomosynthesis x-ray images. Although described with respect to specified methods of converting dimensionality, it should be understood that the modeling component 140 may convert the dimensionality of the first medical imaging data to the second medical imaging data using any suitable or relevant technique or combination of techniques.

At operation 250, the imaging component 120 generates a set of synthetic images having the second imaging type. The set of synthetic images are generated from the first medical imaging data based on the modeled second medical imaging data. The set of synthetic images are generated to a specification defined by the parameter set. For example, where the parameter set includes a specified resolution and sensitivity, the set of synthetic images each have a resolution and sensitivity defined by the parameter set.

Figure 3:
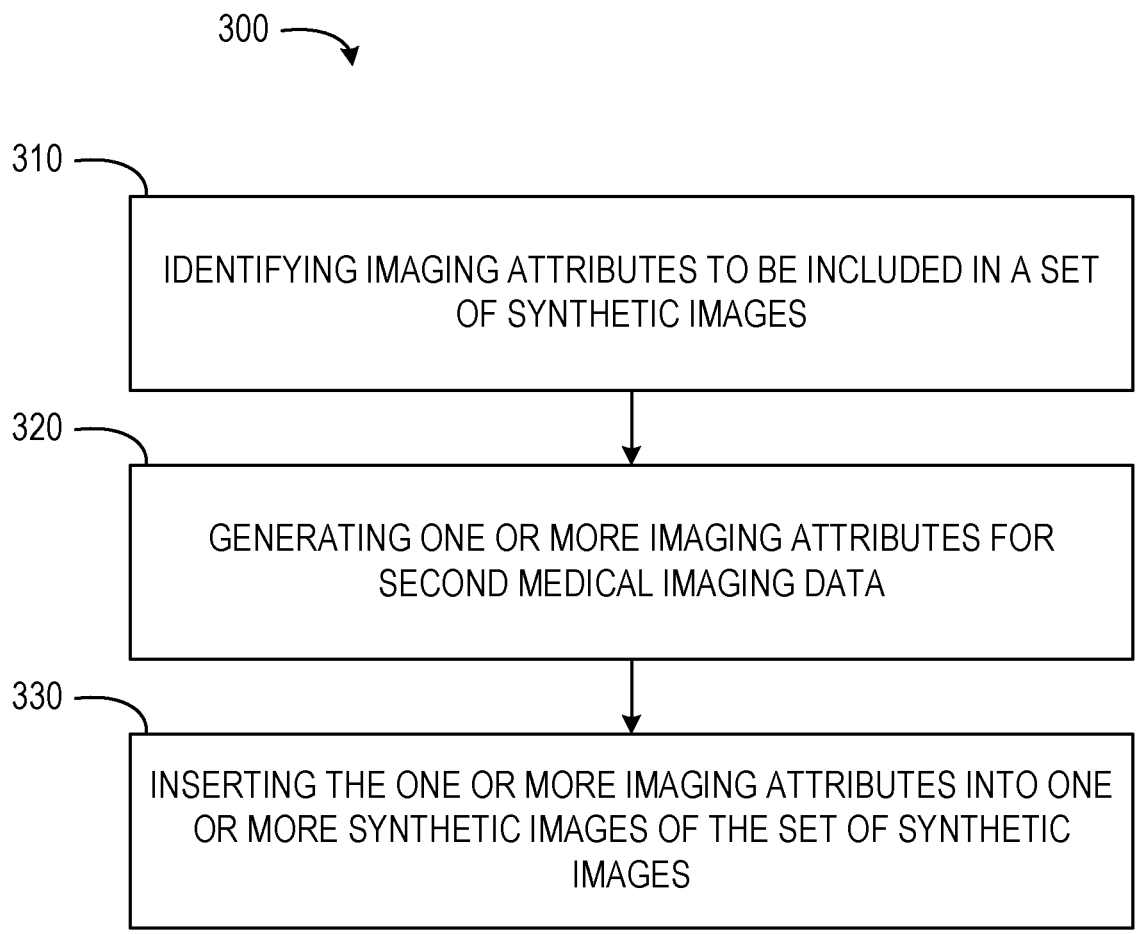
FIG. 3 depicts a flow diagram of a computer-implemented method for disease simulation in synthetic projection imagery, according to at least one embodiment.

FIG. 3 shows a flow diagram of an embodiment of a computer-implemented method 300 disease simulation in synthetic projection imagery. The method 300 may be performed by or within the computing environment 100. In some embodiments, the method 300 comprises or incorporates one or more operations of the method 200. In some instances, operations of the method 300 may be incorporated as part of or sub-operations of the method 200.

In operation 310, the imaging component 120 identifies imaging attributes to be included in the set of synthetic images. The imaging attributes may correspond to selected batches of synthetic images to be generated. The imaging component 120 may also identify random attributes for inclusion in the set of synthetic images. Randomization may be established through user selection. The imaging component 120 may also perform stepwise parameter changes to attributes for inclusion in the set of synthetic images or a plurality of sets of synthetic images. The imaging component 120 may identify imaging attributes to support bulk or batch generation of a set or sets of synthetic images.

In some embodiments, imaging attributes represent medical imaging abnormalities, diseases, indicators of disease, indicators of damage, combinations thereof, or other suitable aspects for conditions able to be diagnosed from a medical image. Further, imaging abnormalities may include patient positioning errors, detector positioning errors, detector/emitter positioning or orientation errors, detector/emitter distance errors, and other imaging errors or irregularities. Additionally, abnormalities may include tissue density and absorption abnormalities. The imaging component 120 may identify imaging attributes from one or more user selections within a user interface presented by the image simulation system 102. In such embodiments, the user may select one or more imaging attributes from a set of imaging attributes (e.g., abnormalities, diseases, or damage). The user may then select a position for the one or more imaging attributes. In absence of one or more location or position selections, the imaging component 120 may identify or select a position or location for the one or more imaging attributes selected by the user. The imaging component 120 may also randomly select imaging attributes or select imaging attributes on a stepwise basis. In such embodiments, the imaging component 120 may generate large batches of simulated medical images with varied imaging attributes from a single source image. In some instances, the imaging attributes selected or applied to each resulting simulated image or batch of simulated images may be tracked and stored in association with the simulated images. The tracked and labeled imaging attributes may act as labeling for model training, generation, tuning, and testing.

In operation 320, the imaging component 120 generates one or more imaging attributes for the second medical imaging data. The one or more imaging attributes may represent one or more medical imaging abnormalities. The imaging component 120 may generate the one or more imaging attributes, at specified or selected positions, using one or more image modification operations. In some embodiments, the imaging component 120 uses image segmentation, warping, shading or other color modification, or other suitable image modification techniques. Where the imaging attributes include tissue absorption or tissue density, the imaging component 120 may generate imaging attributes using ray trace emulation. For example, tissue absorption modeling, as used in NM SPECT and PET for correction of radio tracer photons from CT images, may be used to emulate different x-ray beam hardness.

The imaging component 120 may generate the one or more imaging attributes by determining one or more modifications to be performed to areas of the second medical imaging data surrounding the one or more imaging attributes. The imaging component 120 may initially define aspects of the one or more imaging attributes such as size, position, orientation, opacity, and other aspects. The imaging component 120 may determine areas around the one or more imaging attributes, and determine aspects for the areas such as blur, distortion, warping, or other suitable aspects. The imaging component 120 may calculate values for each aspect of the one or more imaging attributes and areas surrounding the one or more imaging attributes. For example, the imaging component 120 may determine opacity values, color values, distortion values, warping values, distortion angles, combinations thereof, and any other suitable values configured to visually represent the one or more imaging attributes and surrounding areas.

In operation 330, the imaging component 120 inserts the one or more imaging attributes into one or more synthetic images of the set of synthetic images. The imaging component 120 may insert the one or more imaging attributes by applying the values determined for the aspects defining the one or more imaging attributes and surrounding areas. In some embodiments, the imaging component 120 inserts values for the aspects into a previously generated synthetic image. The imaging component 120 may also insert values for the aspects into synthetic images, as the synthetic images are generated.

As described above, certain types of diseases, abnormalities, damage, or other identifiable conditions may be simulated within the set of synthetic images or differing sets of synthetic images. In some embodiments, the one or more imaging attributes, representing diseases or abnormalities, can be simulated in the first imaging data prior to generating the set of synthetic images. In such embodiments, the imaging component 120 may determine values for aspects of the one or more imaging attributes and surrounding areas based on a dimensionality and imaging type of the first imaging data. The imaging component 120 may then insert or apply the values within the first imaging data. Once the values are applied, the imaging component 120 may convert the first imaging data into the set of synthetic images of the second imaging type, as discussed above with respect to the methods 200 and 300. In these embodiments, each source image or source image set (e.g., the first imaging data) corresponds to a separate set of synthetic images. Each source image or set of source images may have one or more elements or attributes inserted. Multiple variations of each source image or set of source images may be generated as an individual set of synthetic images.

Figure 4:
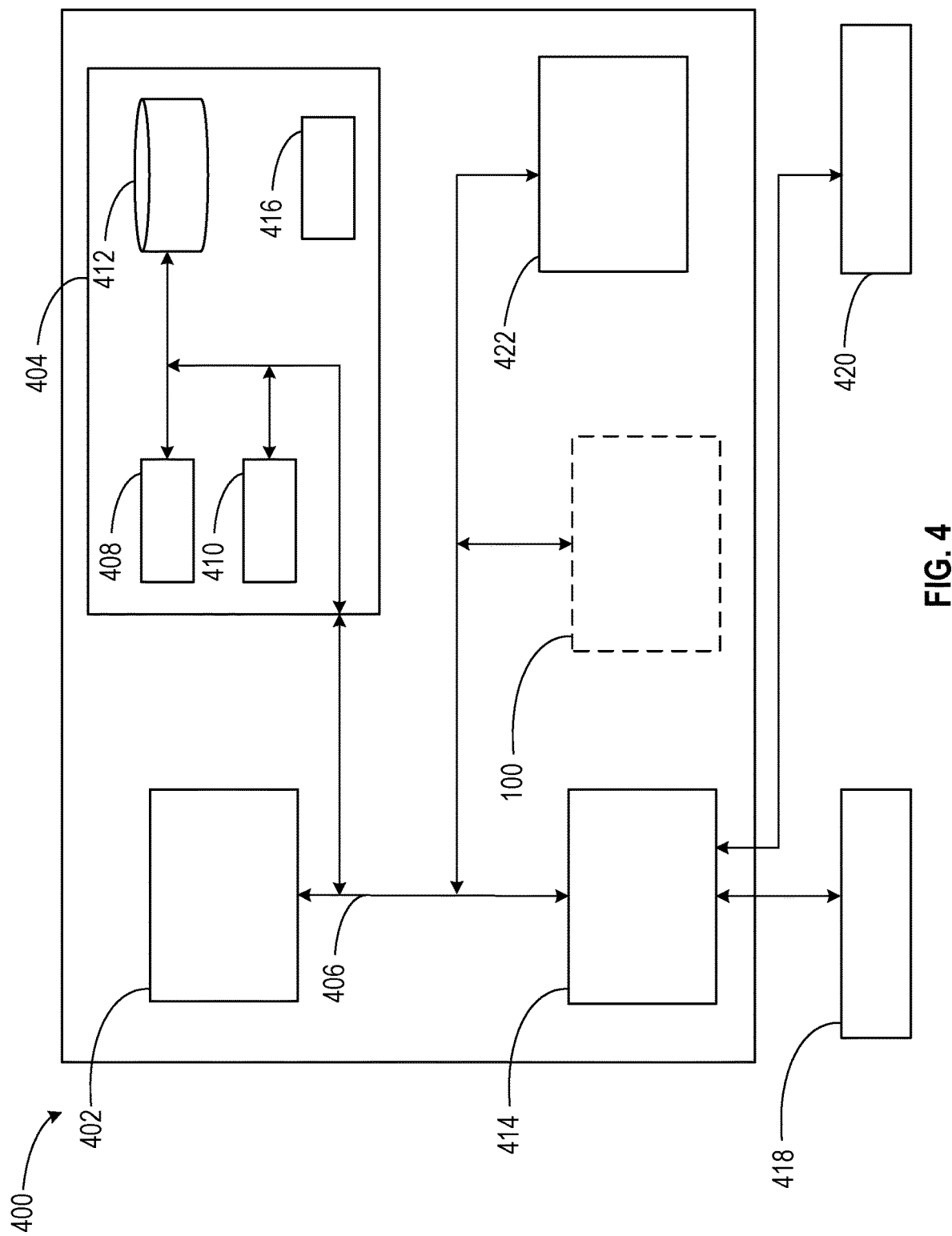
FIG. 4 depicts a block diagram of a computing system for disease simulation in synthetic projection imagery, according to at least one embodiment.

Embodiments of the present disclosure may be implemented together with virtually any type of computer, regardless of the platform being suitable for storing and/or executing program code. FIG. 4 shows, as an example, a computing system 400 (e.g., cloud computing system) suitable for executing program code related to the methods disclosed herein and disease simulation in synthetic projection imagery.

The computing system 400 is only one example of a suitable computer system and is not intended to suggest any limitation as to the scope of use or functionality of embodiments of the present disclosure described herein, regardless, whether the computer system 400 is capable of being implemented and/or performing any of the functionality set forth hereinabove. In the computer system 400, there are components, which are operational with numerous other general purpose or special purpose computing system environments or configurations. Examples of well-known computing systems, environments, and/or configurations that may be suitable for use with computer system/server 400 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server 400 may be described in the general context of computer system-executable instructions, such as program modules, being executed by a computer system 400. Generally, program modules may include routines, programs, objects, components, logic, data structures, and so on that perform particular tasks or implement particular abstract data types. Computer system/server 400 may be practiced in distributed cloud computing environments where tasks are performed by remote processing devices that are linked through a communications network. In a distributed cloud computing environment, program modules may be located in both, local and remote computer system storage media, including memory storage devices.

As shown in the figure, computer system/server 400 is shown in the form of a general-purpose computing device. The components of computer system/server 400 may include, but are not limited to, one or more processors 402 (e.g., processing units), a system memory 404 (e.g., a computer-readable storage medium coupled to the one or more processors), and a bus 406 that couple various system components including system memory 404 to the processor 402. Bus 406 represents one or more of any of several types of bus structures, including a memory bus or memory controller, a peripheral bus, an accelerated graphics port, and a processor or local bus using any of a variety of bus architectures. By way of example, and not limiting, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server 400 typically includes a variety of computer system readable media. Such media may be any available media that is accessible by computer system/server 400, and it includes both, volatile and non-volatile media, removable and non-removable media.

The system memory 404 may include computer system readable media in the form of volatile memory, such as random-access memory (RAM) 408 and/or cache memory 410. Computer system/server 400 may further include other removable/non-removable, volatile/non-volatile computer system storage media. By way of example only, a storage system 412 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 406 by one or more data media interfaces. As will be further depicted and described below, the system memory 404 may include at least one program product having a set (e.g., at least one) of program modules that are configured to carry out the functions of embodiments of the present disclosure.

The program/utility, having a set (at least one) of program modules 416, may be stored in the system memory 404 by way of example, and not limiting, as well as an operating system, one or more application programs, other program modules, and program data. Program modules may include one or more of the access component 110, the imaging component 120, the parameter component 130, and the modeling component 140, which are illustrated in FIG. 1. Each of the operating systems, one or more application programs, other program modules, and program data or some combination thereof, may include an implementation of a networking environment. Program modules 416 generally carry out the functions and/or methodologies of embodiments of the present disclosure, as described herein.

The computer system/server 400 may also communicate with one or more external devices 418 such as a keyboard, a pointing device, a display 420, etc.; one or more devices that enable a user to interact with computer system/server 400; and/or any devices (e.g., network card, modem, etc.) that enable computer system/server 400 to communicate with one or more other computing devices. Such communication can occur via Input/Output (I/O) interfaces 414. Still yet, computer system/server 400 may communicate with one or more networks such as a local area network (LAN), a general wide area network (WAN), and/or a public network (e.g., the Internet) via network adapter 422. As depicted, network adapter 422 may communicate with the other components of computer system/server 400 via bus 406. It should be understood that, although not shown, other hardware and/or software components could be used in conjunction with computer system/server 400. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Service models may include software as a service (SaaS), platform as a service (PaaS), and infrastructure as a service (IaaS). In SaaS, the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. In PaaS, the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. In IaaS, the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment models may include private cloud, community cloud, public cloud, and hybrid cloud. In private cloud, the cloud infrastructure is operated solely for an organization. It may be managed by the organization or a third party and may exist on-premises or off-premises. In community cloud, the cloud infrastructure is shared by several organizations and supports specific community that has shared concerns (e.g., mission, security requirements, policy, and compliance considerations). It may be managed by the organizations or a third party that may exist on-premises or off-premises. In public cloud, the cloud infrastructure is made available to the general public or a large industry group and is owned by an organization selling cloud services. In hybrid cloud, the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling modularity, and semantic interoperability. At the heart of cloud computing is an infrastructure that includes a network of interconnected nodes.

Figure 5:
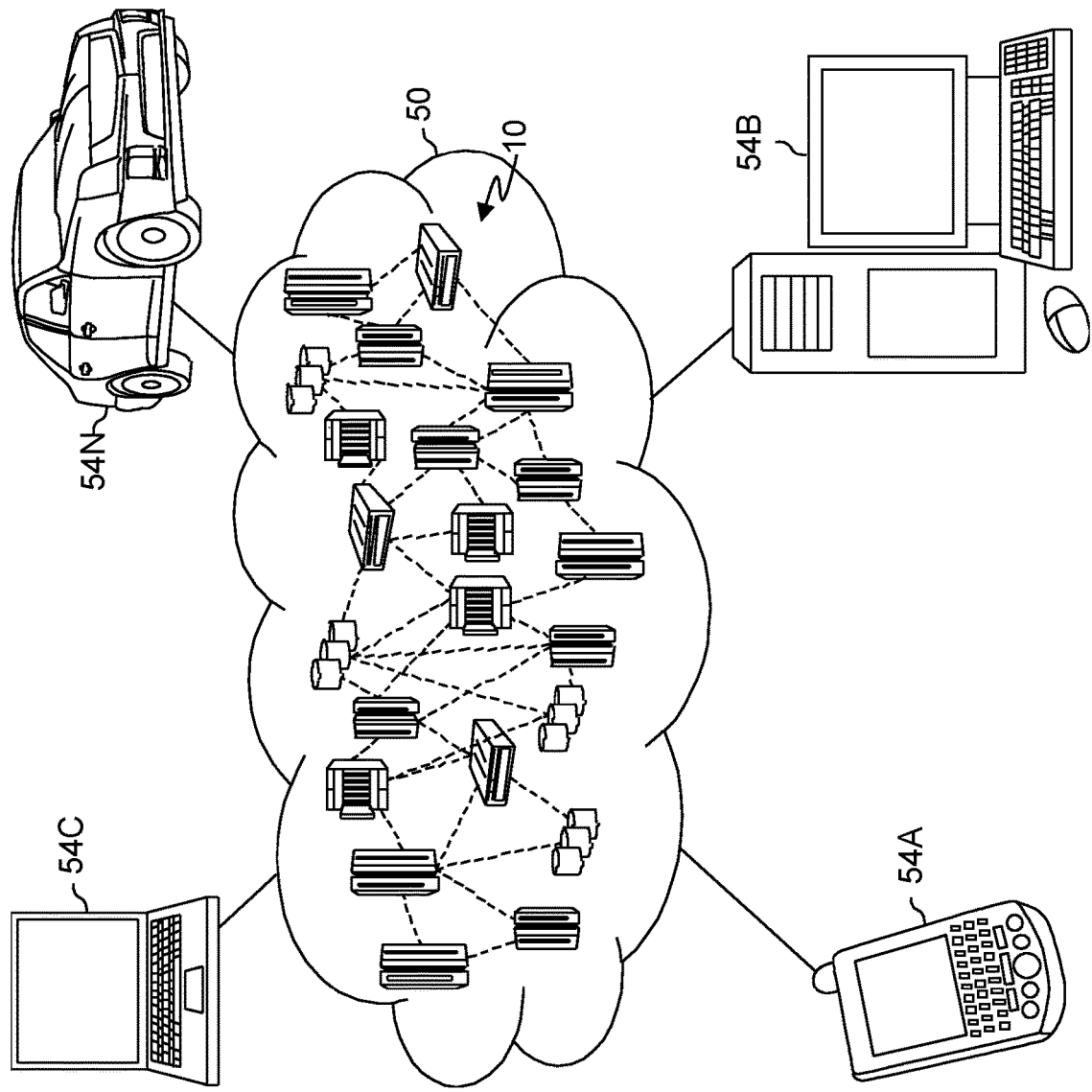
FIG. 5 is a schematic diagram of a cloud computing environment in which concepts of the present disclosure may be implemented, in accordance with an embodiment of the present disclosure.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
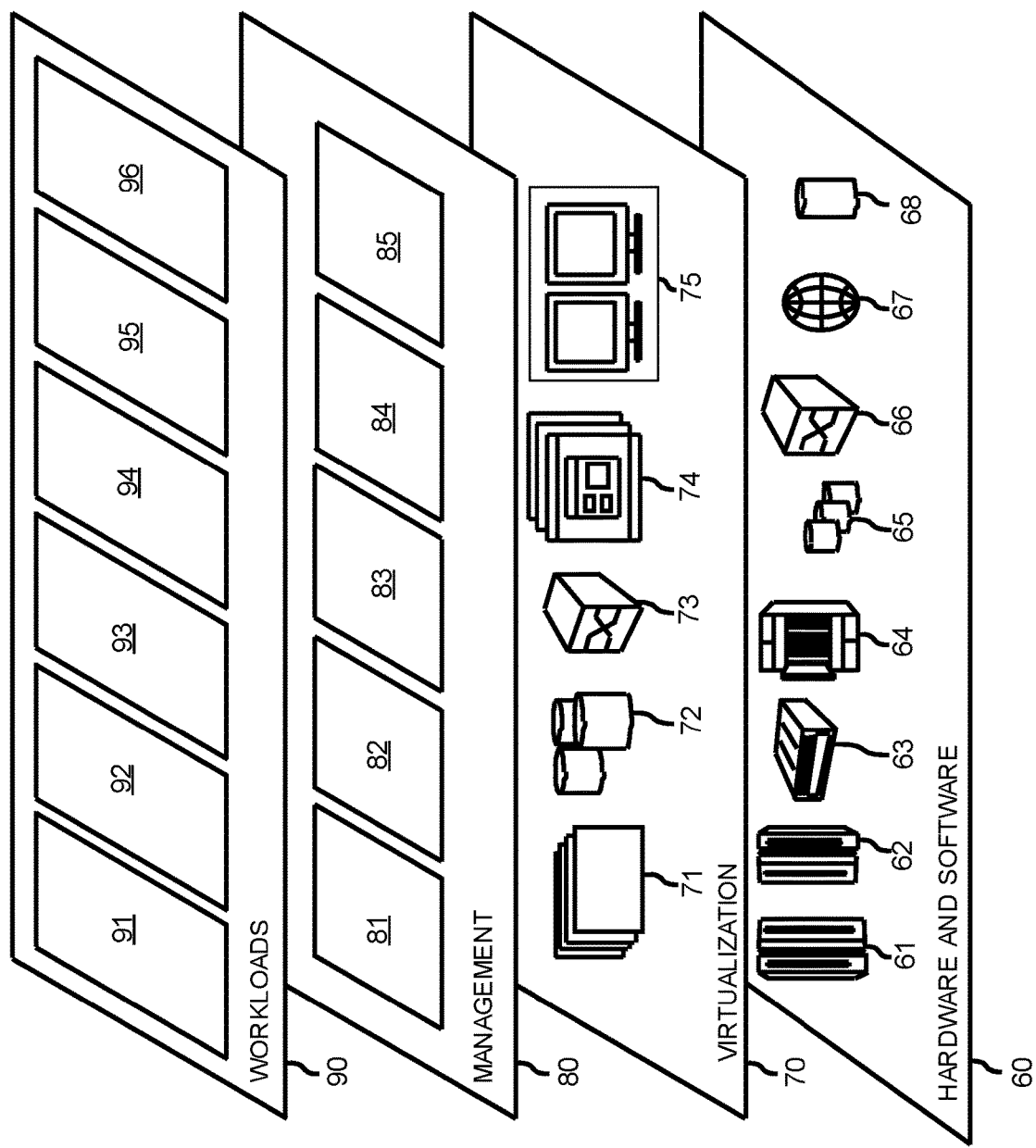
FIG. 6 is a diagram of model layers of a cloud computing environment in which concepts of the present disclosure may be implemented, in accordance with an embodiment of the present disclosure.

Referring now to FIG. 6, a set of functional abstraction layers provided by cloud computing environment 50 (FIG. 5) is shown. It should be understood in advance that the components, layers, and functions shown in FIG. 5 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and network traffic direction processing 96.

Cloud models may include characteristics including on-demand self-service, broad network access, resource pooling, rapid elasticity, and measured service. In on-demand self-service a cloud consumer may unilaterally provision computing capabilities such as server time and network storage, as needed automatically without requiring human interaction with the service's provider. In broad network access, capabilities are available over a network and accessed through standard mechanisms that promote use by heterogeneous thin or thick client platforms (e.g., mobile phones, laptops, and PDAs). In resource pooling, the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). In rapid elasticity, capabilities can be rapidly and elastically provisioned, in some cases automatically, to quickly scale out and rapidly released to quickly scale in. To the consumer, the capabilities available for provisioning often appear to be unlimited and can be purchased in any quantity at any time. In measured service, cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

The descriptions of the various embodiments of the present disclosure have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer-readable storage medium (or media) having computer readable program instructions thereon for causing a processor to carry out aspects of the present invention.

The computer-readable storage medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer-readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatuses, or another device to cause a series of operational steps to be performed on the computer, other programmable apparatus or other device to produce a computer implemented process, such that the instructions which execute on the computer, other programmable apparatuses, or another device implement the functions/acts specified in the flowchart and/or block diagram block or blocks.

The flowcharts and/or block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the present disclosure. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present disclosure has been presented for purposes of illustration and description, but is not intended to be exhaustive or limited to the present disclosure in the form disclosed. Many modifications and variations will be apparent to those of ordinary skills in the art without departing from the scope of the present disclosure. The embodiments are chosen and described in order to explain the principles of the present disclosure and the practical application, and to enable others of ordinary skills in the art to understand the present disclosure for various embodiments with various modifications, as are suited to the particular use contemplated.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method, comprising:
    obtaining first medical imaging data of a first imaging type as source imaging data, the first medical imaging data includes a single first medical image;
    identifying a second imaging type to be generated from the source imaging data, the second imaging type identified from a selection within a user interface prompt responsive to obtaining the first medical imaging data of the first imaging type, the second imaging type selected from a plurality of imaging types;
    identifying a parameter set for the second imaging type based on one or more selections of a user, the parameter set including parameters representing attributes of the second imaging type and parameters of a target imaging device to control creation of images of the second imaging type from the first medical imaging data from the first imaging type;
    modeling a set of second medical imaging data of the second imaging type from the first medical imaging data of the first imaging type based on the parameter set, the set of second medical imaging data modeled using a plurality of values for the parameter set to emulate differing capture settings of the target imaging device;
    generating one or more imaging attributes for the second medical imaging data, the one or more imaging attributes including one or more medical imaging abnormalities representing aspects for conditions able to be diagnosed from a medical image;
    generating a set of synthetic images from the first medical imaging data based on the modeled set of second medical imaging data, the set of synthetic images having the second imaging type and generated to a specification defined, at least in part, by the plurality of values for the parameter set; inserting the one or more imaging attributes into one or more synthetic images of the set of synthetic images to generate a set of training images; and training a neural network image analysis model using the training images.

2. The computer-implemented method of claim 1, wherein the first imaging type is distinct from the second imaging type, the first imaging type being volumetric computerized tomography scan data and the second imaging type being tomosynthesis x-ray data.

3. The computer-implemented method of claim 1, wherein the first imaging type is distinct from the second imaging type, the first imaging type being volumetric computerized tomography scan data and the second imaging type being x-ray data.

4. The computer-implemented method of claim 1, wherein the one or more imaging attributes include one or more medical imaging abnormalities representing image capture errors.

5. The computer-implemented method of claim 1, wherein modeling the second medical imaging data converts a first dimensionality of the first medical imaging data to a second dimensionality of the second medical imaging data.

6. The computer-implemented method of claim 5, wherein the first medical imaging data is three-dimensional imaging data and the second medical imaging data is two-dimensional imaging data.

7. A system, comprising:
one or more processors; and
a computer-readable storage medium, coupled to the one or more processors, storing program instructions that, when executed by the one or more processors, cause the one or more processors to perform operations comprising:
obtaining first medical imaging data of a first imaging type as source imaging data, the first medical imaging data includes a single first medical image;
identifying a second imaging type to be generated from the source imaging data, the second imaging type identified from a selection within a user interface prompt responsive to obtaining the first medical imaging data of the first imaging type, the second imaging type selected from a plurality of imaging types;
identifying a parameter set for the second imaging type based on one or more selections of a user, the parameter set including parameters representing attributes of the second imaging type and parameters of a target imaging device to control creation of images of the second imaging type from the first medical imaging data from the first imaging type;
modeling a set of second medical imaging data of the second imaging type from the first medical imaging data of the first imaging type based on the parameter set, the set of second medical imaging data modeled using a plurality of values for the parameter set to emulate differing capture settings of the target imaging device;
generating one or more imaging attributes for the second medical imaging data, the one or more imaging attributes including one or more medical imaging abnormalities representing aspects for conditions able to be diagnosed from a medical image;
generating a set of synthetic images from the first medical imaging data based on the modeled set of second medical imaging data, the set of synthetic images having the second imaging type and generated to a specification defined, at least in part, by the plurality of values for the parameter set; inserting the one or more imaging attributes into one or more synthetic images of the set of synthetic images to generate a set of training images; and training a neural network image analysis model using the training images.

8. The system of claim 7, wherein the first imaging type is distinct from the second imaging type, the first imaging type being volumetric computerized tomography scan data and the second imaging type being tomosynthesis x-ray data.

9. The system of claim 7, wherein the first imaging type is distinct from the second imaging type, the first imaging type being volumetric computerized tomography scan data and the second imaging type being x-ray data.

10. The system of claim 7, wherein the one or more imaging attributes include one or more medical imaging abnormalities representing image capture errors.

11. The system of claim 7, wherein modeling the second medical imaging data converts a first dimensionality of the first medical imaging data to a second dimensionality of the second medical imaging data.

12. The system of claim 11, wherein the first medical imaging data is three-dimensional imaging data and the second medical imaging data is two-dimensional imaging data.

13. A computer program product comprising a computer readable storage medium having program instructions embodied therewith, the program instructions being executable by one or more processors to cause the one or more processors to perform operations comprising:
obtaining first medical imaging data of a first imaging type as source imaging data, the first medical imaging data includes a single first medical image;
identifying a second imaging type to be generated from the source imaging data, the second imaging type identified from a selection within a user interface prompt responsive to obtaining the first medical imaging data of the first imaging type, the second imaging type selected from a plurality of imaging types;
identifying a parameter set for the second imaging type based on one or more selections of a user, the parameter set including parameters representing attributes of the second imaging type and parameters of a target imaging device to control creation of images of the second imaging type from the first medical imaging data from the first imaging type;
modeling a set of second medical imaging data of the second imaging type from the first medical imaging data of the first imaging type based on the parameter set, the set of second medical imaging data modeled using a plurality of values for the parameter set to emulate differing capture settings of the target imaging device;
generating one or more imaging attributes for the second medical imaging data, the one or more imaging attributes including one or more medical imaging abnormalities representing aspects for conditions able to be diagnosed from a medical image;
generating a set of synthetic images from the first medical imaging data based on the modeled set of second medical imaging data, the set of synthetic images having the second imaging type and generated to a specification defined, at least in part, by the plurality of values for the parameter set; inserting the one or more imaging attributes into one or more synthetic images of the set of synthetic images to generate a set of training images; and training a neural network image analysis model using the training images.

14. The computer program product of claim 13, wherein the first imaging type is distinct from the second imaging type, the first imaging type being volumetric computerized tomography scan data and the second imaging type being tomosynthesis x-ray data.

15. The computer program product of claim 14, wherein the first imaging type is distinct from the second imaging type, the first imaging type being volumetric computerized tomography scan data and the second imaging type being x-ray data.

16. The computer program product of claim 13, wherein the one or more imaging attributes include one or more medical imaging abnormalities representing image capture errors.

17. The computer program product of claim 13, wherein modeling the second medical imaging data converts three-dimensional imaging data to two-dimensional medical imaging data.

* * * * *